United States Patent
Nuvula et al.

(10) Patent No.: US 9,932,388 B2
(45) Date of Patent: Apr. 3, 2018

(54) CHROMATOGRAPHIC PROCESS FOR PRODUCING HIGH PURITY FIBRINOGEN AND THROMBIN

(71) Applicant: HEMARUS THERAPEUTICS LIMITED, Hyderabad (IN)

(72) Inventors: Ashok Kumar Nuvula, Hyderabad (IN); Mitali Samaddar, Hyderabad (IN); Neelima Vadde, Hyderabad (IN); Zinia Chakraborty, Hyderabad (IN); Swapna Sagar Duggineni, Hyderabad (IN); Uma Devi Komath, Hyderabad (IN)

(73) Assignee: Hemarus Therapeutics Limited, Hyderabad (IN)

( * ) Notice: Subject to any disclaimer, the term of this patent is extended or adjusted under 35 U.S.C. 154(b) by 0 days.

(21) Appl. No.: 14/883,574

(22) Filed: Oct. 14, 2015

(65) Prior Publication Data

US 2016/0137719 A1    May 19, 2016

(30) Foreign Application Priority Data

Nov. 13, 2014   (IN) .......................... 5704/CHE/2014

(51) Int. Cl.
  *C07K 14/75*   (2006.01)
  *A61L 24/10*   (2006.01)
  *A61L 24/02*   (2006.01)
  *C12N 9/74*    (2006.01)

(52) U.S. Cl.
  CPC .............. *C07K 14/75* (2013.01); *A61L 24/02* (2013.01); *A61L 24/106* (2013.01); *A61L 24/108* (2013.01); *C12N 9/6429* (2013.01); *C12Y 304/21005* (2013.01)

(58) Field of Classification Search
  None
  See application file for complete search history.

(56) References Cited

U.S. PATENT DOCUMENTS

| | | |
|---|---|---|
| 4,022,758 A | 5/1977 | Andersson et al. |
| 4,427,650 A | 1/1984 | Stroetmann |
| 5,138,034 A | 8/1992 | Uemura et al. |
| 5,290,918 A | 3/1994 | Bui-Khac |
| 5,354,682 A | 10/1994 | Kingdon et al. |
| 5,395,923 A | 3/1995 | Bui-Khac et al. |
| 5,716,645 A | 2/1998 | Tse et al. |
| 5,739,288 A | 4/1998 | Edwardson et al. |
| 5,792,835 A | 8/1998 | Tse et al. |
| 5,834,420 A | 11/1998 | Laub et al. |
| 5,907,032 A | 5/1999 | MacGregor et al. |
| 5,981,254 A | 11/1999 | Bui-Khac |
| 6,037,457 A | 3/2000 | Lord |
| 6,245,548 B1 | 6/2001 | Ralston et al. |
| 6,960,463 B2 | 11/2005 | Kanellos et al. |
| 7,550,567 B2 | 6/2009 | Metzner et al. |
| 7,816,495 B2 | 10/2010 | Kingsland et al. |
| 8,012,728 B2 | 9/2011 | Metzner et al. |
| 2006/0134769 A1 | 6/2006 | Connolly et al. |
| 2012/0195953 A1 | 8/2012 | Hoang |
| 2013/0274444 A1 | 10/2013 | Schulz et al. |
| 2014/0154231 A1 | 6/2014 | Nogre et al. |

FOREIGN PATENT DOCUMENTS

| | | |
|---|---|---|
| AU | 199332064 | 8/1993 |
| AU | 2001023311 | 7/2001 |
| CA | 1041424 | 10/1978 |
| CN | 1207064 | 4/2003 |
| CN | 102295696 | 12/2011 |
| DE | 19824306 | 11/1999 |
| EP | 0439156 | 7/1991 |
| WO | 1997026280 A1 | 7/1997 |

OTHER PUBLICATIONS

Matsuda et al., (Thrombosis Res., 1972, vol. 1, issue 6, pp. 619-630).*
Lee et al. (Protein Expression and Purification, vol. 43, 2005, pp. 10-17).*
Chen et al. (PNAS, vol. 72, 1975, pp. 1132-1136).*
J Thorac Cardiovasc. Surg., Apr. 1998, 883-889, 115(4).
Biomaterials, 2003, 321-327, 24.
Ann Clin Lab Sci Winter 2001, 08-118, vol. 31, No. 11.

* cited by examiner

*Primary Examiner* — Hope Robinson
(74) *Attorney, Agent, or Firm* — Harita S. Achanta

(57) ABSTRACT

The present invention relates to a chromatographic process for obtaining purified fibrinogen and thrombin from human plasma. The purified fibrinogen and thrombin preparations contain plasminogen in amounts less than 1 ug/mL. The low levels of plasminogen eliminates use of a proteolytic inhibitor, such as aprotinin in fibrin sealant kits which are used for human therapeutic applications.

9 Claims, 4 Drawing Sheets

FIG. 2A: SDS-PAGE analysis of Fibrinogen - Component-1: Human Fibrinogen

FIG. 2B: SDS-PAGE profile of Thrombin - Component-2: Human Thrombin

FIG. 3: Plasminogen levels in preparations made as described herein versus the market brands from competitors

| | Plasminogen levels | | |
|---|---|---|---|
| Present invention | Competitor – 1 Market brand | Competitor – 2 Market brand | Fresh plasma |
| < 1 ug /mL | ~100 µg/mL | ~29.2µg/mL | ~ 200ug / mL |

CHROMATOGRAPHIC PROCESS FOR PRODUCING HIGH PURITY FIBRINOGEN AND THROMBIN

FIELD OF THE INVENTION

The present invention relates to the field of therapeutic protein purification from human plasma. In one aspect, the present invention relates to improved processes for manufacturing fibrinogen and thrombin in high purity through chromatography. Another aspect of the present invention relates to a fibrin sealant kit consisting of purified thrombin and fibrinogen.

BACKGROUND ART

During wound healing, fibrin clot is considered as the final step in the coagulation cascade. The process of forming a fibrin clot involves conversion of fibrinogen to fibrin monomers by thrombin (Factor IIa) and cross linking of these fibrin monomers to form a fibrin polymer in the presence of Factor XIII. The resulting fibrin clot acts as a hemostatic plug to seal of the capillaries at the site of injury. During surgical procedures, fibrin sealants are used to aid the surgical closure procedures.

Bergel discovered fibrin's physiological gluing properties in 1909. Since then fibrin has been used as an adhesive. However, it was the clotting property of whole blood that was used and not purified Fibrin. In 1944, Cronkite used fibrinogen component from blood along with thrombin to secure a skin graft but, the low concentrations of fibrinogen and thrombin in the preparation failed to give a good quality clot. In 1975, Maitras was the first to use a concentrated preparation of Fibrinogen for this purpose. Since then the synthetic glues have been increasingly replaced by biological glues. The biological surgical sutures are effective, easy to use and reasonably well tolerated by the patients, but its viral safety, adhesiveness and absence of toxicity to adjacent tissues are the problems still being addressed to varying extents.

The commercial kits consists of components of clot formation like fibrinogen, thrombin, calcium chloride, and an anti-fibrinolytic, typically a plasmin inhibitor. The anti-fibrinolytic (like aprotinin) helps to prevent early degradation of the fibrin clot that may be brought about by plasmin contamination in the fibrinogen-thrombin preparations.

There are several patents in the prior art that disclose processes for the preparation and compositions of concentrates of Fibrinogen and Thrombin in biological glues. Few deal with processes for the preparation of Fibrinogen and Thrombin separately as individual proteins and a few others discuss their processes together as components of a fibrin sealant kit, which mainly involve precipitation of fibrinogen from plasma by the addition of organic solvents or salts at defined concentrations, pH and temperature conditions.

U.S. Pat. No. 5,290,918 and U.S. Pat. No. 5,395,923 disclose processes for the preparation of a protein concentrate coagulable by thrombin, and containing mostly fibrinogen, endogenous Factor XIII and fibronectin. This purification process does not involve any chromatography step.

U.S. Pat. No. 7,550,567 discloses a process for purifying fibrinogen, comprising one or more process steps in which one or more contaminating proteins are depleted by negative chromatography and/or negative adsorption using cation exchanger, hydrophobic gel and/or dye gel. However, absence of plasminogen contamination in the preparation to avoid the use of a protease inhibitor in the Fibrin sealant kit and the final purity levels were not discussed.

WO1997026280A1 discloses a process for the recovery of fibrinogen from a fibrinogen-containing material by affinity. But the plasminogen levels are not quantified in the final preparations.

The second major component in the fibrin sealant kit is Thrombin. Thrombin is obtained by proteolytic cleavage of prothrombin. Purification processes in literature generally describe the purification of prothrombin from plasma and a final single step comprising proteolytic conversion of purified prothrombin to thrombin. Several processes for the purification of prothrombin have been disclosed in prior art. Some of the related patent prior art disclose processes involving protein precipitation alone by addition of salts or other chemicals in one or more steps, while a few other patents disclosed a combination of protein precipitation followed by single or multiple chromatography steps.

U.S. Pat. No. 5,354,682 discloses the purification and recovery of human thrombin produced in commercial-scale quantities. EP 0439156 discloses a process for the production of a liquid thrombin wherein a combination of anion exchange followed by cation exchange chromatography is employed for the purification. U.S. Pat. No. 8,012,728 discloses a process for the preparation of thrombin which is stable in the liquid state. U.S. Pat. No. 5,981,254 discloses a process of preparing biological glue. US 20060134769 discloses a process for the preparation of virus-inactivated thrombin. U.S. Pat. No. 6,245,548 discloses a process for converting pure prothrombin or prothrombin free of other coagulating factors to thrombin by treating prothrombin with sodium citrate. U.S. Pat. No. 5,907,032 discloses a process for the production of thrombin particularly human thrombin that are capable of being produced in a freeze-dried form. The final purity of thrombin and the absence of plasminogen in the preparations have not been elaborated in these patents.

The processes relating to fibrin sealant kits have also been disclosed in prior art, with the kits being made of components like fibrinogen, thrombin, calcium chloride and aprotinin, a protease inhibitor for the preparation of a biological glue. This is exemplified in the inventions described in U.S. Pat. No. 4,427,650, U.S. Pat. No. 5,716,645, U.S. Pat. No. 5,290,918, U.S. Pat. No. 5,395,923, U.S. Pat. No. 5,739,288 and U.S. Pat. No. 5,981,254. Most of the preparations described in the prior art on Fibrin sealant kits are found to be using aprotinin as the anti-fibrinolytic agent to prevent premature lysis of the clot from the contaminating plasminogen in the fibrinogen/thrombin preparations.

Avoiding the use of bovine or synthetic aprotinin can eliminate the risk of hypersensitivity reactions that are known to occur upon repeated exposures to aprotinin as described in a study published in the J Thorac Cardiovasc. Surg. 1998 April; 115(4):883-9). In this, the authors have described a subgroup of patients who developed aprotinin-specific antibodies after topical aprotinin application. The authors suggest that any use of aprotinin in patients should be documented and patients with pre-exposure to aprotinin in any form must be carefully monitored to avoid unexpected anaphylactic reactions. They have even questioned the necessity of adding aprotinin as a stabilizing agent in fibrin sealants. A similar conclusion was drawn by another group that studied the adverse effects of fibrinolysis inhibitor aprotinin in wound healing after suturing tissues with fibrin glue (Biomaterials 24 (2003) 321-327). They showed that even liver tissue which is known to have high fibrinolytic activity was sealed and repaired well in the absence of plasminogen inhibitors. On the contrary, if aprotinin was added, the non-degraded matrix remained in the tissue even after 15 days and affected migration of repair cells. They concluded that the presence of the fibrinolysis inhibitor in the fibrin glue application was detrimental to wound healing.

There are many patents in the prior art—U.S. Pat. No. 7,816,495, U.S. Pat. No. 5,834,420, U.S. Pat. No. 4,022,758, US20130274444, CA 1041424, U.S. Pat. No. 5,792,835, CN 102295696, U.S. Pat. No. 5,138,034, AU 2001023311, DE 19824306, U.S. Pat. No. 6,960,463, U.S. Pat. No. 6,037,457, US 20120195953, AU 199332064, CN 1207064, US 20140154231, U.S. Pat. No. 6,960,463, U.S. Pat. No. 6,960,463, DE19824306, which disclosed purification of fibrin or purification of thrombin but many of them have not disclosed the levels of the contaminants in the final products.

SUMMARY OF THE INVENTION

There is a requirement for purifying fibrinogen and thrombin in a combination of chromatography steps to obtain final purified preparations that have extremely low (less than 1 ug/mL) or undetectable levels of the contaminant, plasminogen. The inventors of the present invention have developed a fibrin sealant kit comprising highly purified preparations of fibrinogen and thrombin with extremely low (less than 1 ug/ml) or undetectable amounts of plasminogen. The sealant is hence a fibrinolysis inhibitor-free kit. By avoiding the use of bovine or synthetic aprotinin, the risk of hypersensitivity reactions that are known to occur upon repeated exposures to aprotinin, can be eliminated.

The present invention discloses an approach to overcome the above challenge of purifying fibrinogen and thrombin with low levels of plasminogen. The present invention describes a complete end-to-end multi-step chromatography process to obtain fibrinogen and thrombin of increased purity. In addition, the process avoids the use of tranexamic acid in free form or bound to affinity matrices, a compound with proven neurotoxic effects. The advantage of these highly purified preparations is that they have minimal or undetectable levels of plasminogen so that these sealant kits can be manufactured by excluding aprotinin.

The present invention relates to a fibrin sealant kit comprising purified fibrinogen and thrombin. The invention particularly relates to purification of fibrinogen and thrombin from human plasma through an all-chromatography process. The fibrinogen and thrombin preparations thus obtained are found to be almost free of the major fibrinolytic contaminant plasminogen.

DESCRIPTION OF TABLES

Figure 1:
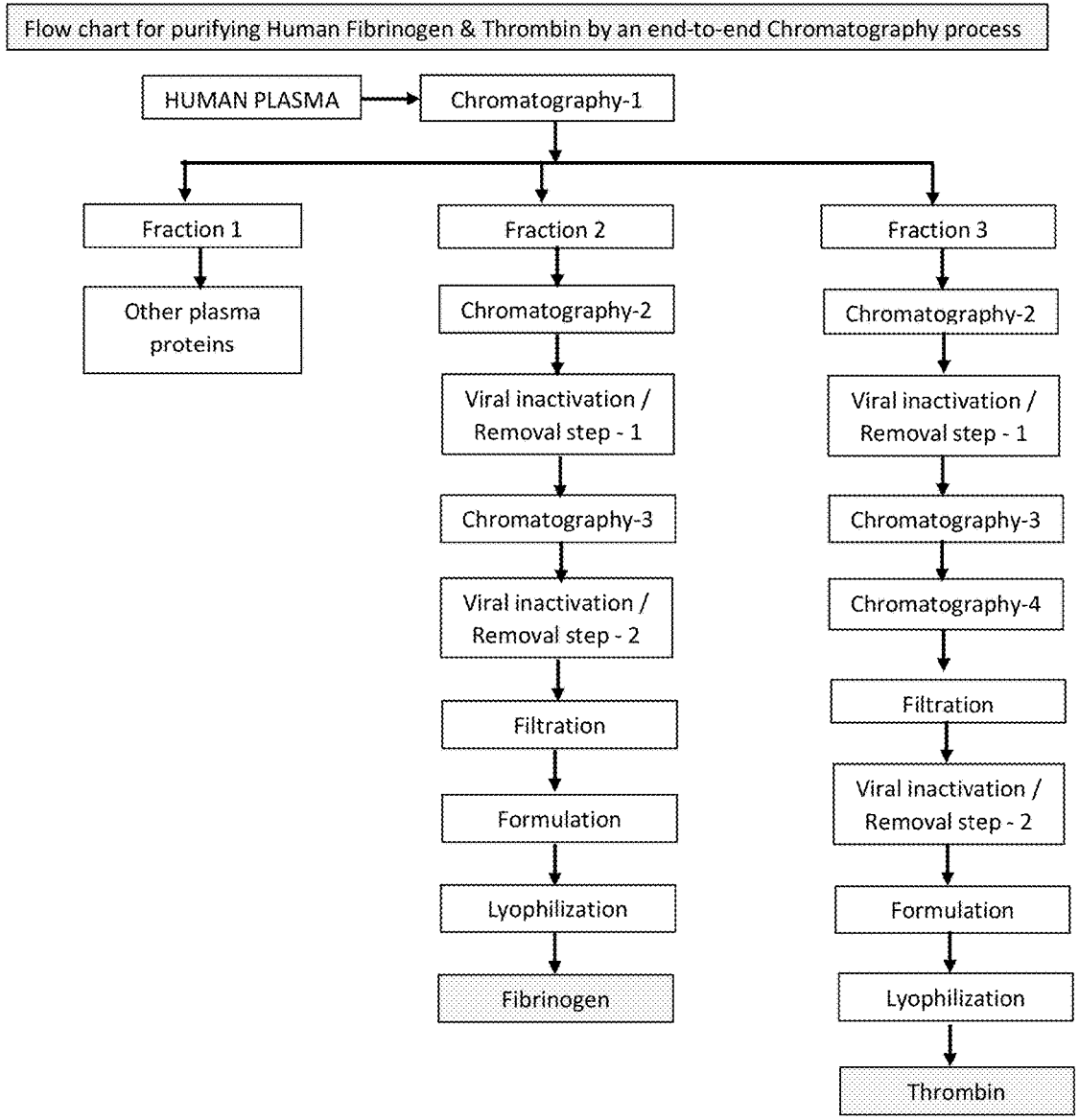
FIG. 1: An outline illustration of a process scheme for simultaneous purification of Fibrinogen and Thrombin by chromatography without the use of an ethanol precipitation step
Figure 2A:
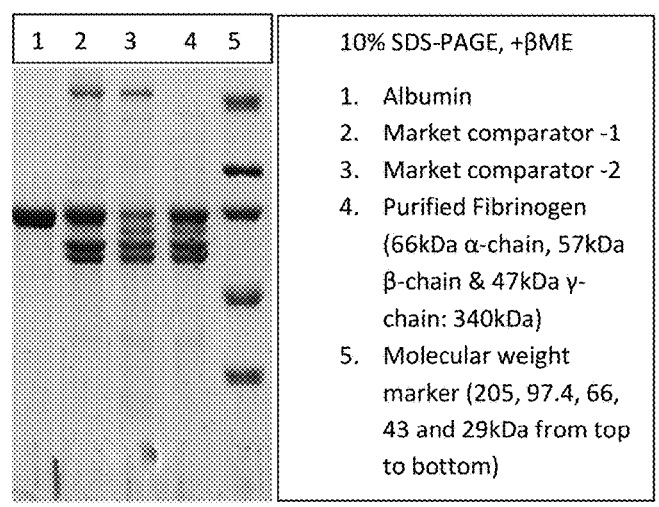
FIG. 2A: SDS-PAGE analysis of Fibrinogen
Figure 2B:
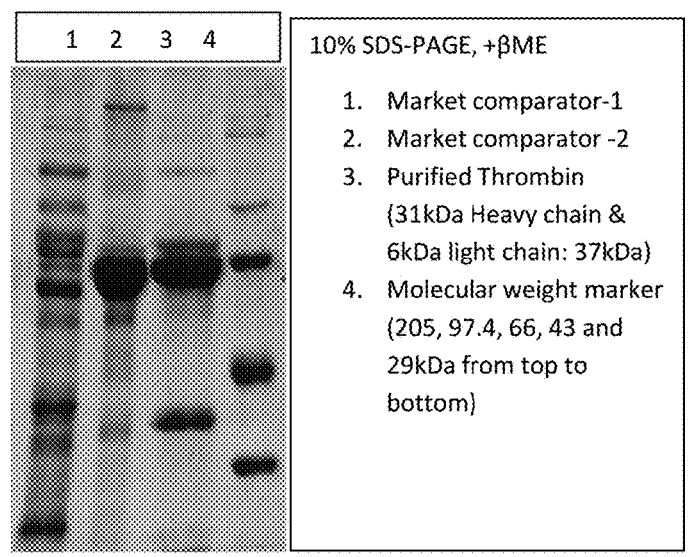
FIG. 2B: SDS-PAGE profile of Thrombin

FIG. 3: Plasminogen levels in preparations of the present invention versus the competitor market brands

DETAILED DESCRIPTION OF THE INVENTION

Fibrin sealant for tissue adhesion has become an important and versatile surgical tool. It is composed primarily of two components, viz., fibrinogen and thrombin. Fibrin sealant acts by mimicking the final stage of the natural clotting mechanism to form a fibrin clot that is broken down by fibrinolysis and reabsorbed by the body naturally over the course of several days. The process by which fibrinogen and thrombin combine in the presence of Factor XIII and calcium chloride to form a fibrin clot has been well described in scientific literature.

Currently, fibrin sealant is used in virtually every surgical specialty. The primary area of usage is cardiovascular surgery, where applications include sealing of complex suture lines, vascular conduits, cannulation sites and vascular anastomoses. In neurosurgery, fibrin sealant is commonly used as an adjunct to dural closures, to reduce post-operative cerebral spinal fluid leakage and in the repair of dural defects. Fibrin sealant is effective in sealing dead spaces left after surgical excision (as in axillary dissection), where there is a potential for serous drainage leading to seroma formation. In general surgery, fibrin sealant is used to achieve hemostasis on raw surfaces of the liver and in reconstruction of the spleen, especially following traumatic injury. There are other documented applications of fibrin sealant in orthopaedic, ophthalmologic, trauma, head and neck, gynecologic, urologic, gastrointestinal, and dental surgeries.

Although commercial fibrin sealant made from pooled plasma-derived human fibrinogen and human thrombin has been available in Europe, Canada and Japan for several years (since 1972 in Europe), the US Food and Drug Administration (FDA) did not approve the commercial product for use in the USA until May 1998. Delay in availability of commercial fibrin sealant in the USA was largely due to concerns over possible viral disease transmission from blood-borne pathogens such as HIV, hepatitis B virus, and hepatitis C virus.

Currently, licensed commercial fibrin sealants contain fibrinogen and thrombin derived from pooled, virally inactivated human plasma. They also contain an anti-fibrinolytic agent, bovine aprotinin. Future generations of fibrin sealant are likely to be free of bovine products due to reported instances (albeit rare) of reactions to bovine aprotinin. Commercial fibrin sealant has been used in >4 million procedures worldwide to date, with only one reported case of suspected viral disease transmission (human parvovirus transmission in Japan). As increasingly sensitive virus detection techniques become available, shortening or even closing the window for infectious donations, and as improved virus inactivation techniques are developed, such as solvent detergent treatment, general acceptance of products derived from pooled plasma may grow. In fact, pooled, virus-inactivated blood products have been shown to be very safe [Ann Clin Lab Sci Winter 2001 vol. 31 no. 1 108-118).

In a preferred embodiment of the invention described herein, the process is characterized by an initial fractionation of the plasma into two, three or more components by a molecular sieve chromatography process using resins from any of the standard chromatography resin manufacturers. The commonly used resins for gel permeation are SEPHACRYL™, SUPEROSE™, SEPHADEX™, SUPERDEX™ CELLUFINE™ among others. The frozen plasma is initially thawed, pooled and filtered to remove particulate matter. The filtered plasma is then fractionated (as Fraction I, II and III) on a gel permeation column (Chromatography-I) which simultaneously removes high molecular weight lipids and lipoproteins from the protein fractions of interest. Fractions II and III obtained after Chromatography-I are the starting materials for the Fibrinogen and Thrombin processes, respectively.

Purification of Fibrinogen:

Step 1(a):

The thawed and pooled plasma after filtration is loaded onto a gel filtration column, packed with any of the commonly used resins such as CELLUFINE™, SEPHAROSE™ or any other commercial brand. Three major fractions (Fraction 1, Fraction 2 and Fraction 3, as in FIG. 1) are obtained after group separation on the column, and packed to a height of 30 to 60 cm. Fraction 1 contains Factor VIII along with a few high molecular weight plasma proteins such as IgM and macroglobulins. Fraction 2 contains Fibrinogen along with certain classes of immunoglobulins, lipoproteins, Transferrin and other proteins in the same size range. Fraction 3 mainly contains Thrombin (in the form of Prothrombin), IgG, Albumin, Factor IX, Anti-Thrombin III and several other proteins of medium to smaller molecular size range. The three fractions—Fraction 1, Fraction 2 and Fraction 3 are also referred to as Fraction I, Fraction II and Fraction III interchangeably in different parts of the text.

Step 1(b):

The column is run in a suitable buffer composed of phosphate, citrate or other similar buffer salts that provide a pH range of 6.5 to 7.5. The buffer salt is at a concentration of 0.05 to 0.5M, preferably less than 150 mM. In addition, the buffer contains additives of salts in suitable quantities to preserve the activity of sensitive proteins. The column is loaded with thawed, pooled and filtered plasma and the three protein fractions (Fraction 1, Fraction 2 and Fraction 3) are collected as shown in FIG. 1.

Step 1(c):

In a preferred embodiment of the invention described herein, the process is characterized by an initial fractionation of the plasma into three components by a molecular sieve chromatography process using resins such as CELLUFINE™ SEPHAROSE™ or any other gel filtration media from any of the standard chromatography resin manufacturers, most preferably SEPHAROSE™. Fraction 2 obtained from the first gel filtration column shown in FIG. 1, is processed for Fibrinogen purification through a multi-step chromatography process. This fraction is loaded onto a hydrophobic interaction chromatography (HIC) column such as PHENYL SEPHAROSE™ (although other hydrophobic resins with ligands of butyl, octyl and related ligands bound to any base matrix other than SEPHAROSE™ may also be used). The HIC column is equilibrated with a buffer containing Tris phosphate or similar salts in the range of 50 mM to 500 mM, containing salts such as ammonium sulphate, sodium sulphate or sodium chloride-like salts generally used in HIC, at a concentration of 0.05M to 0.5M in the pH range of 6.5 to 7.5. The column is eluted with the same buffer but containing reduced concentration of a salt such as ammonium sulphate in the pH range of 7.0 to 8.0.

Step 1(d):

The eluate containing fibrinogen from the HIC column of Step 1(c), is subjected to a Solvent/Detergent (S/D) treatment with 1% TRITON™ X 100 and 0.3% TNBP [tri (n-butyl) phosphate] for 4 to 6 hrs for viral inactivation. The virally inactivated sample is further purified by loading it onto an anion exchange resin (such as DEAE (diethyl aminoethyl), Q (Quarternary ammonium) or other similar ligands bound to chromatography resins such as SEPHAROSE™).

Step 1(e):

The treated solution from step 1(d) is subjected to an anion exchange column which is equilibrated with Tris phosphate or similar salts in a concentration range of 10 mM to 150 mM containing sodium chloride in the range of 10 mm to 150 mM in the pH range of 6.5 to 7.5. This column is then washed with suitable buffer and fibrinogen is eluted with a buffer containing the same salts as the equilibration buffer but at a higher concentration of sodium chloride in the range of 50 mM to 200 mM in the same pH range.

Step 1(f):

The ion exchange eluate obtained from step 1(e) containing purified fibrinogen is collected and subjected to pasteurization at 60° C. for 10 hrs for viral inactivation.

Step 1(g):

This is buffer exchanged with a solution containing the formulation excipients and the final formulated solution of Fibrinogen is subjected to sterile filtration and freeze drying. Upon reconstitution, the purified fibrinogen contains over 95% clottable protein and has a clear appearance. This is one of the components of the Fibrin sealant kit.

Step 1(h):

The formulated fibrinogen obtained from step 1(g) is subjected to lyophilization before filling into the vials. The yield of the finally obtained fibrinogen is in the range of 25 mg to 150 mg per liter of plasma. The pH range of fibrinogen solution is in the range of 6.5 to 7.5.

Purification of Thrombin:

Step 2(a):

In a preferred embodiment of this invention, Thrombin is purified from Fraction-3 (FIG. 1) obtained as described in Step 1(a).

Step 2(b):

Fraction-3 containing prothrombin is loaded onto an anion exchange column containing ligands such as DEAE or Q bound to chromatography resins such as SEPHAROSE™ SEPHADEX™ or other chromatography resins. The eluate from anion exchange column is loaded onto an affinity resin which is heparin bound to a resin such as SEPHAROSE™. The buffer used is citrate or phosphate buffer in the molarity range of 0.01M to 0.1M, and the pH range of 6.5 to 8.5. The sample is loaded and eluted in the same buffer with increasing amounts of sodium chloride (0 to 0.5M). The eluate from this column contains Prothrombin along with other vitamin K dependant proteins and this is further processed for the purification of Thrombin.

Step 2(c):

The first anion exchange column eluate fraction containing prothrombin (from Step 2(b)) is subjected to a viral inactivation procedure, by the addition of solvent/detergent (S/D), which is 1% TWEEN™-80 and 0.3% TNBP [tri (n-butyl) phosphate], for 4 to 6 hrs.

Step 2(d):

The sample obtained from step 2(c) is loaded onto heparin SEPHAROSE™ and purified prothrombin is collected by elution using a buffer containing increasing amounts of NaCl (0 to 0.5M) and $CaCl_2$ (0 to 50 mM).

Step 2(e):

The prothrombin obtained at the end of the step in Step 2(d) is bound to an anion exchange column in the pH range of 6 to 9, equilibrated with Tris phosphate or other suitable buffers in the molarity range of 5 to 100 mM. In the presence of equilibration buffer, viz., buffer containing calcium chloride (1-50 mM), the bound prothrombin is allowed to undergo on-column cleavage to thrombin at temperatures of 4° C. to 28° C. for 50 to 70 hrs.

Step 2(f):

Thrombin is eluted from the column by increasing the sodium chloride concentration in the column buffer in the range of 0 to 0.5M and the eluate is subjected to nanofiltration for virus removal using any of the standard commercially available nanofilters. This process yields thrombin in the range of 100,000 IU per liter of plasma.

Step 2(g):

The thrombin obtained from step 1(g) is subjected to formulation and lyophilization before filling into the vials. The activity in the vial after formulation is between 400 to 800 IU per ml (and optionally an additional vial of Thrombin at a lower strength in the range of 2 to 10 IU/ml). This vial is one of the components in the fibrin sealant kit. The pH of thrombin solution is in the range of 6.5 to 7.5.

Human Plasminogen present as a contaminant in human fibrinogen preparations is estimated using a quantitative ELISA based method. Plasminogen binds to anti-human plasminogen antibody coated on a 96-well microtitre plate. In the next step, the polyclonal anti-human plasminogen primary antibody is allowed to bind to the captured plasminogen antigen on the microtitre well. The bound polyclonal antibody reacts with a specific secondary antibody conjugated to horseradish peroxidase (HRP). The presence of plasminogen in the preparation is detected using a chromogenic substrate TMB (3,3',5,5'-Tetramethylbenzidine). The intensity of the color developed (i.e. the quantity of plasminogen present) is determined by measuring the absorbance at 450 nm wavelength, after stopping the reaction using sulfuric acid. At a defined linear range of concentration of Plasminogen, the amount of color developed is proportional to the concentration of the Plasminogen antigen. Using an appropriate certified reference standard for the standard curve, the quantity of plasminogen in fibrinogen preparation can be determined.

The Fibrin sealant kits prepared using the purified Thrombin and Fibrinogen components of the present invention have been found to have very low (less than 1 ug/mL) or undetectable amounts of plasminogen contamination. The levels of plasminogen in fresh plasma is around 200 ug/mL. When few competitor brands of fibrin sealant kits available in the market were tested, they were found to contain plasminogen levels in the range of 29 ug/mL to 100 ug/mL (Table 1).

The Fibrin Sealant Kit of the present invention comprises the following components:

Fibrinogen—25 mg to 150 mg per ml—reconstituted in 1 mL of Water for Injection (WFI), Thrombin—400 to 800 IU per ml (and optionally an additional vial of Thrombin at a lower strength in the range of 2 to 10 IU/ml)—reconstituted in 1 mL of 40 mM $CaCl_2$, 1 mL WFI vial, 1 mL 20 to 60 uM $CaCl_2$ vial.

A representative Table 1 below indicates the levels of plasminogen in some of the most popular fibrin sealant kits in the market. The purity of the fibrinogen obtained by the present invention is enhanced compared to the products from competitors that are available in the market.

It was observed that the product prepared using the process of the present invention exhibited an activity of greater than 0.1 million IU of Thrombin per liter of plasma and a specific activity of greater 3000 IU/mg of protein. This is higher than the reported yield and specific activity values (1500 to 2500 IU/mg) in published literature. Similarly for Fibrinogen, the yield was 25 to 150 mg/liter of plasma with clottable protein equal to 100%, whereas the other procedures gave lesser yields and clottable protein which were close to 70%.

The fibrin sealant kit described in the present invention comprises highly purified preparations of fibrinogen and thrombin. Fibrinogen and Thrombin of the present invention show purities greater than 98% by SDS-PAGE and HPLC analysis. The Fibrinogen preparation has extremely low (less than 1 ug/ml) or undetectable amounts of plasminogen contaminant. This is advantageous as it helps in omitting a component of the kit, a plasminogen inhibitor such as aprotinin. The sealant is hence a fibrinolysis inhibitor-free kit.

The invention claimed is:

1. A chromatographic process for the isolation and purification of fibrinogen and thrombin, obtained from human plasma, without the use of ethanol precipitation, that contains plasminogen in amounts less than 1 ug/mL, comprising:
   i. subjecting said human plasma to gel filtration chromatography to obtain three fractions (Fraction I, Fraction II and Fraction III);
   ii. subjecting Fraction II and Fraction III to additional chromatography steps for purification; and
   iii. subjecting to viral inactivation and recovering isolated purified fibrinogen from Fraction II and recovering isolated purified thrombin from Fraction III.

2. The chromatographic process of claim 1, wherein purification of the fibrinogen from said Fraction II, further comprises:
   a) adding ammonium sulphate to Fraction II to a concentration of 0.05M to 0.5M;
   b) loading onto a hydrophobic interaction chromatography (HIC) column to obtain eluate with plasminogen in amounts of less than 1 ug/mL;
   c) conducting solvent/detergent (S/D) virus inactivation for the eluate obtained from step b; and
   d) subjecting the treated eluate from step c to anion exchange chromatography for recovering purified fibrinogen.

3. The chromatographic process of claim 1, wherein purification of thrombin from said Fraction III, further comprises:
   a) loading the Fraction III onto an anion exchange column equilibrated with a buffer comprising an acetate or citrate, with a molarity of 0.01M to 0.1M in the pH range of 6.5 to 8.5, eluting a partially purified prothrombin with buffer containing sodium chloride, to obtain prothrombin with plasminogen in amounts of less than 1 ug/mL;
   b) conducting solvent-detergent (S/D) virus inactivation and loading onto an affinity column for the capture of prothrombin and removal of S/D;
   c) collecting purified prothrombin eluate by elution with a buffer containing increasing amount of sodium chloride ranging from 0 to 0.5M;
   d) subjecting the eluate from step c to an anion exchange in the pH range of 6 to 9 in a buffer containing 1 to 50 mM concentration of calcium chloride, at 4° C. to 28° C. temperature for 50 to 70 hours for the conversion of prothrombin to thrombin; and
   e) subjecting the treated eluate obtained from step d to nanofiltration for virus removal and recovering purified thrombin.

4. The chromatographic process of claims 1-3, wherein the purified fibrinogen and thrombin having plasminogen in amounts of less than 1 ug/mL, eliminates use of aprotinin, a proteolytic inhibitor, in a fibrin sealant kit.

5. The fibrin sealant kit of claim 4, wherein the concentration of fibrinogen is 25-150 mg/ml.

6. The fibrin sealant kit of claim 4, wherein the concentration of thrombin is 400 to 800 IU/ml.

7. The fibrin sealant kit of claim 6, wherein the fibrin sealant kit optionally comprises an additional vial of thrombin at a lower strength in the range of 2 to 10 IU/ml.

8. The fibrin sealant kit of claim 5, further comprising a source of calcium, which is calcium chloride.

9. The fibrin sealant kit of claim 8, wherein the amount of calcium chloride is in the range of 20 to 60 uM.

* * * * *